United States Patent [19]

Wilkes et al.

[11] Patent Number: 5,458,835
[45] Date of Patent: Oct. 17, 1995

[54] PROCESS OF MAKING VISCOSE STAPLE FIBERS

[75] Inventors: Andrew G. Wilkes; Alan J. Bartholomew, both of Coventry, United Kingdom

[73] Assignee: Courtaulds PLC, United Kingdom

[21] Appl. No.: 279,504

[22] Filed: Jul. 22, 1994

Related U.S. Application Data

[62] Division of Ser. No. 230,881, Apr. 20, 1994, which is a continuation of Ser. No. 965,623, Oct. 22, 1992, abandoned, which is a continuation of Ser. No. 680,597, Mar. 29, 1991, abandoned, which is a continuation of Ser. No. 226,046, Jul. 29, 1988, abandoned.

[30] Foreign Application Priority Data

Jul. 30, 1987 [GB] United Kingdom ............... 8718081

[51] Int. Cl.⁶ ........................... D01D 5/253; D01F 2/08
[52] U.S. Cl. ................ 264/143; 264/177.13; 264/188; 264/191; 264/198; 264/233; 264/234
[58] Field of Search ........................ 264/143, 177.13, 264/188, 191, 198, 211.14, 211.17, 233, 234

[56] References Cited

U.S. PATENT DOCUMENTS

| | | |
|---|---|---|
| 1,773,969 | 8/1930 | Dreyfus et al. . |
| 2,002,153 | 5/1935 | Mendel . |
| 3,670,069 | 6/1972 | Mitchell et al. . |
| 3,676,420 | 7/1972 | Fulton et al. . |
| 3,702,778 | 11/1972 | Mueller et al. . |
| 3,889,678 | 6/1975 | Chatterjee et al. . |
| 3,986,511 | 10/1976 | Olofsson et al. . |
| 4,076,933 | 2/1978 | Turbak et al. . |
| 4,081,884 | 4/1978 | Johst et al. . |
| 4,129,679 | 12/1978 | Woodings . |
| 4,165,743 | 8/1979 | Denning . |
| 4,187,342 | 2/1980 | Holst et al. . |
| 4,242,405 | 12/1980 | Bockno . |

(List continued on next page.)

FOREIGN PATENT DOCUMENTS

| | | |
|---|---|---|
| 32597 | 7/1981 | European Pat. Off. . |
| 89071 | 9/1983 | European Pat. Off. . |
| 329375 | 8/1989 | European Pat. Off. . |
| 369259 | 5/1990 | European Pat. Off. . |
| 1491169 | 6/1969 | Germany . |
| 2018071 | 2/1971 | Germany . |
| 156049 | 6/1971 | New Zealand . |
| 318631 | 8/1930 | United Kingdom . |
| 1307001 | 2/1973 | United Kingdom . |
| 1333047 | 10/1973 | United Kingdom . |
| 1387915 | 3/1975 | United Kingdom . |
| 1393778 | 5/1975 | United Kingdom . |
| 1470465 | 4/1977 | United Kingdom . |

(List continued on next page.)

OTHER PUBLICATIONS

E. Treiber, "Stretching, Drawing and Modified Cross-Section in Viscose Spinning", Chemiefasern, 5:344–348 (1967) (English translation).
E. Treiber, "Stand und Entwicklungen bei Viskosefaserstoffen", Cellulose Chemistry and Technology, 2:53–66 (1968).
E. Treiber et al, "Kring Forskning och Utveckling—Die neue Universal—Laboratoriumsspinnmaschine am schivedischen Holzforsclungsinstitut", Svensk Papperstidning, 10:344–347 (May 31, 1970).
R. Moncrieff, "Man–made Fibres", 5th edition, Heywood Books, p. 179 (1970).

(List continued on next page.)

Primary Examiner—Leo B. Tentoni
Attorney, Agent, or Firm—Howson and Howson

[57] ABSTRACT

Viscose filaments, preferably in staple fibre form, which have a decitex of less than 5.0 and a multi-limbed cross-section, the limbs having a length-to-width aspect ratio of at least 2:1. Examples of multi-limbed cross-sectional shapes are Y-, X-, H- and T-shapes. The fibre can be formed into woven, non-woven or knitted fabrics, and is especially useful for absorbent products.

28 Claims, 5 Drawing Sheets

U.S. PATENT DOCUMENTS

| | | |
|---|---|---|
| 4,245,000 | 1/1981 | Bockno . |
| 4,362,159 | 12/1982 | Sakurai et al. . |
| 4,388,260 | 6/1983 | Bockno . |
| 4,402,899 | 9/1983 | Hartmann et al. . |
| 4,525,565 | 6/1985 | Laisney et al. . |
| 4,627,849 | 12/1986 | Walton et al. . |
| 4,661,101 | 4/1987 | Sustmann . |
| 4,973,623 | 11/1990 | Haugsby et al. . |
| 5,171,235 | 12/1992 | Theis et al. . |
| 5,358,679 | 10/1994 | Parekh et al. ............ 264/177.13 |
| 5,364,383 | 11/1994 | Hayes et al. . |

FOREIGN PATENT DOCUMENTS

| | | |
|---|---|---|
| 2042970 | 10/1980 | United Kingdom . |
| 1581727 | 12/1980 | United Kingdom . |
| 2085304 | 4/1982 | United Kingdom . |
| 2094637 | 9/1982 | United Kingdom . |
| 2141436 | 12/1984 | United Kingdom . |
| 80/00554 | 4/1980 | WIPO . |
| 89/01062 | 2/1989 | WIPO . |
| WO89/07925 | 9/1989 | WIPO . |
| WO89/07924 | 9/1989 | WIPO . |

OTHER PUBLICATIONS

Albin F. Turbak, "Solvent Spun Rayon, Modified Cellulose Fibers and Derivatives," *ACS Symposiium Series 58*, Meeting of the American Chemical Society, New Orleans, La., Mar. 21 to 23, 1977—Chapters 4 and 6 only.

J. Gordon Cook, "Man–Made Fibres," *Handbook of Textile Fibres,* Merrow Publ. Co. Ltd., 4th Edition (1968) pp. 58–59 and 77–78 only.

The Textile Institute, "Textile Terms and Definitions," 8th Edition, ed. Beech et al, (Sep. 1988)—pp. 200, 273 and 297 only.

R. W. Moncrieff, "Man–Made Fibres," *Heywood Books,* 5th Edition (1970)—pp. 272–273 only.

Kirk–Othmer, Encyclopedia of Chemical Technology, 3rd Edition, vol. 19, p. 855 (Sep. 1982).

J. Ratcliffe et al, "Courtaulds Develops Specialised Non–Woven Fibres," *Nonwovens Yearbook,* Aug. 1984, pp. 1, 28, 30.

Wagner, "Die Textilen Rohstoffe," Deutscher Fachverlag, Frankfort, 6th Edition, Feb. 1981, pp. 156–157 (and partial English translation of these pages).

Opposition Papers filed by Dr. Albin Schwarz on behalf of Lensing Aktiengesellschaft, dated Mar. 12, 1993.

Opposition Papers filed by W. Wehnert on behalf of Hoechst AG, dated Mar. 12, 1993.

K. Gotze, *Chemiefasern, nach dem Viskoseverfahren,* Springer–Verlag, Publ., Berlin, p. 641 (1967).

Translation of Japan 61–113,812 (Published May 31, 1986).

PROCESS OF MAKING VISCOSE STAPLE FIBERS

This is a divisional of application Ser. No. 08/230,881 filed on Apr. 20, 1994, which is a continuation of Ser. No. 07/965,623 filed on Oct. 22, 1992 now abandoned, which is a continuation of Ser. No. 07/680,597 filed on Mar. 29, 1991 (now abandoned), which is a continuation of Ser. No. 07/226,046 filed on Jul. 29, 1988 (now abandoned).

This invention relates to regenerated cellulosic filaments, particularly viscose filaments, which have a multi-limbed cross-section, to fibre comprising such filaments and to products formed therefrom.

One advantage of multi-limbed viscose filaments over conventional circular cross-sectional viscose filaments is their greater bulk, because the circumferential area of the multi-limbed filaments is larger than their actual cross-sectional area. For example, Japanese Patent Application Kokai 61-113812 describes a filament yarn consisting of X-or &-shaped continuous viscose filaments that is used in textile applications where bulk is important, for example in pile weaves.

Another advantage of multi-limbed viscose filaments is their increased absorbency over conventional filaments. Thus, multi-limbed filaments in staple fibre from are particularly useful for absorbent products, for example tampons, towels and swabs. Absorbent viscose fibre is described in UK Patent 1 333 047 in which the filaments have a collapsed hollow structure and a multi-limbed cross-section. Although these filaments have a relatively high absorbency compared with conventional viscose filaments they have the disadvantage that they are complicated to manufacture as the filaments must be formed with an inflated, hollow structure and subsequently collapsed. The process also has the disadvantage that the collapse of the fibre is difficult to control sufficiently to ensure a uniform filament cross-section, and therefore the resulting filaments have irregular multi-limbed cross-sectional shapes. The filaments also have a relatively low tenacity.

The present invention provides a solid filament of regenerated cellulosic material having a decitex of less than 5.0 and a multi-limbed cross-section, each limb having a length-to-width aspect ratio of at least 2:1.

The length-to-width aspect ratio of the filament limbs is generally from 2:1 to 10:1, preferably from 2:1 to 7:1, and more preferably from 3:1 to 5:1. In general, the higher the aspect ratio, the higher the degree of free volume of the filaments. This gives a high degree of absorbency when the filaments are in staple fibre form, provided that the limbs are not so long and thin that they bend back upon themselves.

The filament according to the invention preferably has 3 or 4 limbs, although it may have more than 4 limbs if desired, and also preferably has a cross-sectional shape that is generally (i.e. largely) symmetrical about at least one axis, as in a Y-, X-, H- or T- shaped filament cross-section, although other shapes are also included within the scope of the invention. Preferably, the filament has a Y-shaped cross-section. The angle between the limbs varies according to the cross-sectional shape and can be, for example, from 5° to 180° although it is preferred that the filament cross-section is as regular as possible.

As mentioned above, the filament according to the invention has a low decitex of less than 5.0, a low decitex being advantageous for high absorbency products. Generally the decitex is between 0.5 and 5.0, but more preferably is between 1.5 and 4.0.

Filaments according to the invention are advantageously produced in the form of staple fibre, and the invention further provides such staple fibre. The combination of the multi-limbed cross-sectional shape and the low decitex gives filaments which in staple fibre form exhibit a high absorbency. Surprisingly, we have found that, although the filaments have a solid structure as opposed to a collapsed hollow structure characteristic of the fibre of UK Patent 1,333,047 mentioned above, the fibre of the invention has an absorbency which can match and in some product forms exceed the absorbency of the fibre of the said UK patent, even though its water imbibition is considerably lower. Usually the fibre according to the invention has a total free absorbency (TFA) of at least 24 grams of water per gram of the fibre using the test as set out in British Pharmacopoeia 1980, Standard Methods (BP 1980, SDM.) XI.A, p. 928. For instance, a TFA in the range up to 28 g/g can be obtained. In addition the fibre of the invention has high bulk, a cotton-like handle, and a tenacity approximately equivalent to conventional circular cross-sectional viscose filaments for a given viscose composition and decitex.

The staple fibre according to the invention preferably comprises multi-limbed filaments substantially all of which have substantially the same cross-sectional shape. This enables the fibre properties, such as absorbency and bulk, to be more readily controlled. However, if desired, the staple fibre may comprise a mixture of filaments of two or more different cross-sectional shapes provided that at least some of the filaments have a multi-limbed cross-section characteristic of the filaments of the invention.

Preferably, the filaments according to the invention are viscose, and they are conveniently spun from a standard viscose composition using standard viscose spinning conditions, with the exception that multi-limbed shaped extrusion holes in the spinnerette are substituted for the conventional circular shaped holes. As the filaments produced have a solid rather than a hollow structure, the disadvantages involved in producing hollow filaments are avoided.

The viscose composition used for spinning the filaments of the invention may be a commonly used viscose, typically having a cellulose content of 5 to 12% by weight and a caustic soda content of 4 to 10%, preferably 5 to 7%, by weight. Filaments may be spun over the full range of salt figures, although viscose having a salt figure of 4.0 to 12.0 is generally used. The ball-fall viscosity of the viscose can be from 15 to 180 seconds at 18° C., but is preferred to be from 45 to 55 seconds.

The filaments are spun through extrusion holes having a multi-limbed shape similar to the desired shape of the filaments. Typically the spinnerette is made from a gold-platinum alloy and the extrusion holes formed by conventional methods such as spark erosion or mechanical punching. To achieve filament limb aspect ratios of at least 2:1 together with a filament decitex of less than 5.0 the dimensions of the limbs of the extrusion holes are preferably between 50 μm and 250 μm long and between 20 μmd 40 μm wide.

The filaments are spun into a spin bath which can conveniently be of a standard spin bath composition for viscose spinning. Typically this composition includes by weight zero to 3%, preferably 0.5 to 2%, zinc sulphate, 6 to 20%, preferably 7 to 10%, sulphuric acid and 10 to 28%, preferably 20 to 26%, sodium sulphate. The spin bath temperature is generally between 50 and 60° C, although higher and lower temperatures may be used.

We have found that, for absorbent products such as tampons, even higher absorbencies can be achieved by adapting the process to give a slower rate of filament regeneration. The regeneration rate can be slowed down by altering one or more or the spinning conditions, for example by decreasing the acid level and/or increasing the sulphate level. Alternatively, or in addition, the viscose can be modified by a viscose modifier which is usually added to the viscose prior to spinning. Any of the commonly available viscose modifiers may be employed, examples being polyalcohols, soluble dithiocarbonates, soluble aliphatic and alicyclic amines, oxyethanols and quinoline. Polyglycols are preferred, especially PEG-1500 (Polyethylene glycol where 1500 indicates the average molecular weight of the chain).

After spinning, the filaments are stretched, and then preferably cut into staple lengths, washed and dried using conventional techniques to give staple fibre.

The low decitex, multi-limbed filaments in staple fibre form can be used in a wide range of textile and other applications which take advantage of the fibre's high absorbency, bulk, cover and/or cotton-like handle. These applications include, for example, tampons, swabs and waddings, woven fabrics, knitted fabrics and non-woven fabrics. Non-woven fabrics can be produced by, for example, latex bonding, powder bonding, thermal bonding or hydro-entanglement. The fibre is especially useful for tampons and similar products because the fibre has the combined advantages of high absorbency and satisfactory compressional stability. In general, tampons are manufactured in one of two forms; longitudinally expanding or radially expanding. For either type the absorbency of the tampon is linked to its stability, in that any modification made to the tampon fibre to increase its absorbency generally has the effect of decreasing its stability. A tampon formed from fibre according to the invention has the advantage that it can be manufactured to have an acceptable stability together with high absorbency.

Thus a longitudinally expanding tampon formed from fibre according to the invention can be manufactured to have a stability of approximately 15 mm as measured by the 'expansion text' as hereinafter defined, and an absorbency of at least 4.3 grams 1% saline solution per gram of fibre, and often at least 4.5 g/g and up to about 5.5 g/g, as measured by a 'modified Syngina' test as hereinafter defined.

Likewise, a radially expanding tampon formed from fibre according to the invention can be manufactured to have a stability of at least 3.2 decaNewtons (daN), often 3.8 daN or more, e.g. up to about 8.0 daN, as measured by the 'crush test' as hereinafter defined, and an absorbency of at least 4.5 g/g, often at least 5.0 g/g and up to about 6.0 g/g, as measured by a 'modified Syngina' test as hereinafter defined.

In addition tampons having a higher stability can be formed from fibre according to the invention. Thus, longitudinally expanding tampons can be manufactured that have a stability of 10 mm or less, and radially expanding tampons can be manufactured having a stability of 5.0 daN or more.

Products formed from the fibre may contain solely fibre according to the invention or may be blended with other fibres. These other fibres may be cellulosic fibres, such as standard viscose or cotton, or non-cellulosic such as polyester. In addition, the fibre of the invention may be incorporated in a product in only one cross-sectional shape, for example solely Y-shaped, or, alternatively, two or more different cross-sectional shapes can be used.

BRIEF DESCRIPTION OF THE DRAWINGS

The invention is illustrated by the following Examples and with reference to the accompanying drawings in which.

All percentages given are by weight unless otherwise specified.

Example 1

Figure 1:
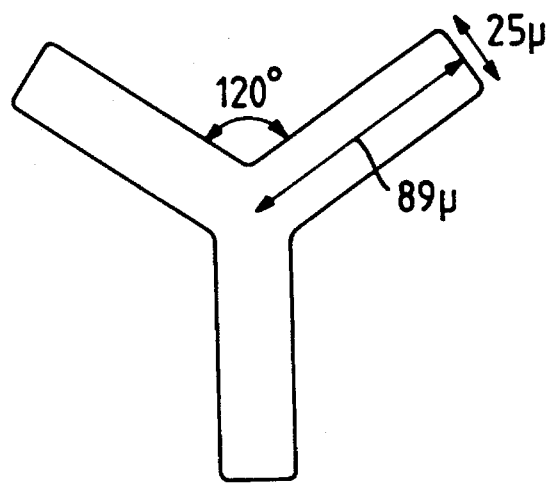
FIGS. 1, 6 and 8 are diagrammatic representations of extrusion holes used for spinning filaments according to the invention.

A 14,364 filament viscose two comprising 9.0% cellulose and 6.0% caustic soda, with a salt figure of 5.6 and a ball-fall viscosity of 45 seconds at 18° C., was spun through Y-shaped extrusion holes, the dimensions of the limbs of the holes being 89 μm long and 25 μm wide with equivalent limb-to-limb angles of 120° as shown diagrammatically in FIG. 1. The filaments were spun into a spin bath comprising 7.5% sulphuric acid, 0.8% zinc sulphate, 24.5% sodium sulphate and 67.2% water to form a tow of filaments having an average filament decitex of 2.2. The spinning speed was 50 m per minute and the viscose extrusion rate was 1068 milliliters per minute (ml/min). The two was stretched by 45% in a 2% aqueous sulphuric acid solution at 95° C., cut to staple lengths of 38 mm and washed and dried.

Figure 4:
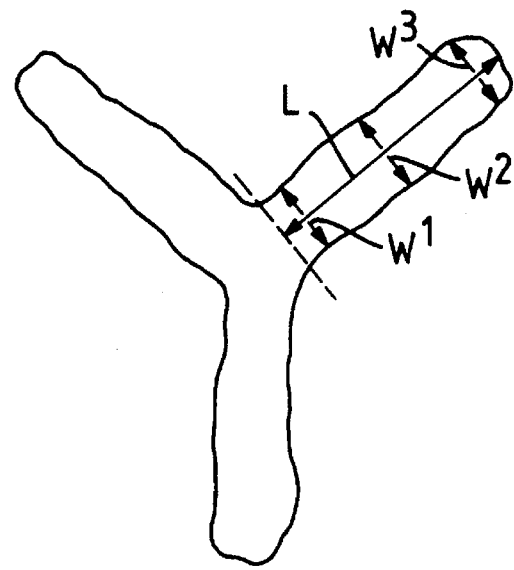
FIG. 4 shows the measurements taken to determine the aspect ratio of a filament limb.
Figure 2:
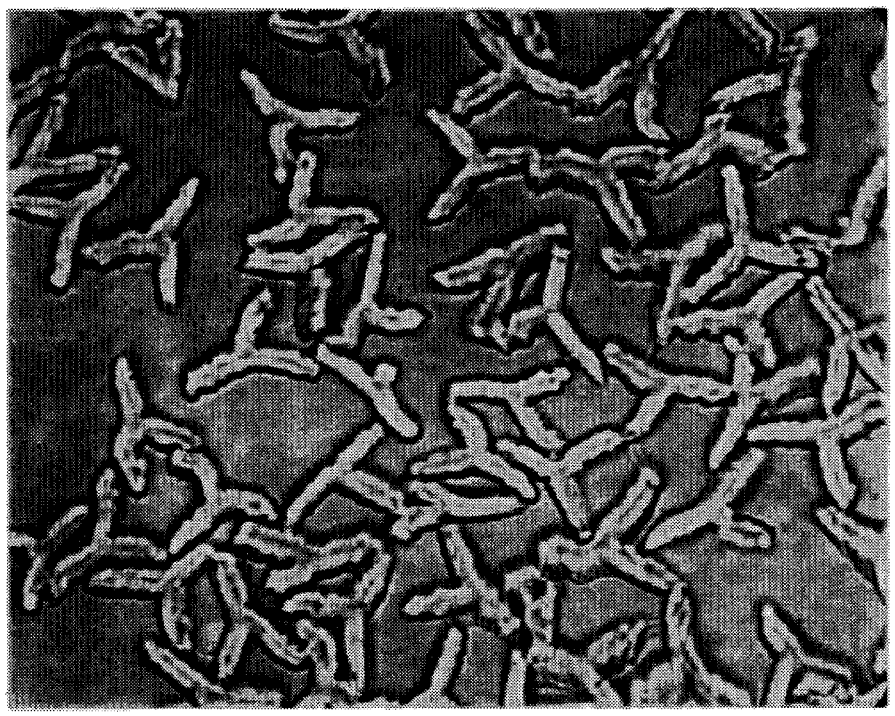
FIGS. 2, 3, 5, 7 and 9 are reproductions of photographs of filament cross-sections.
Figure 3:
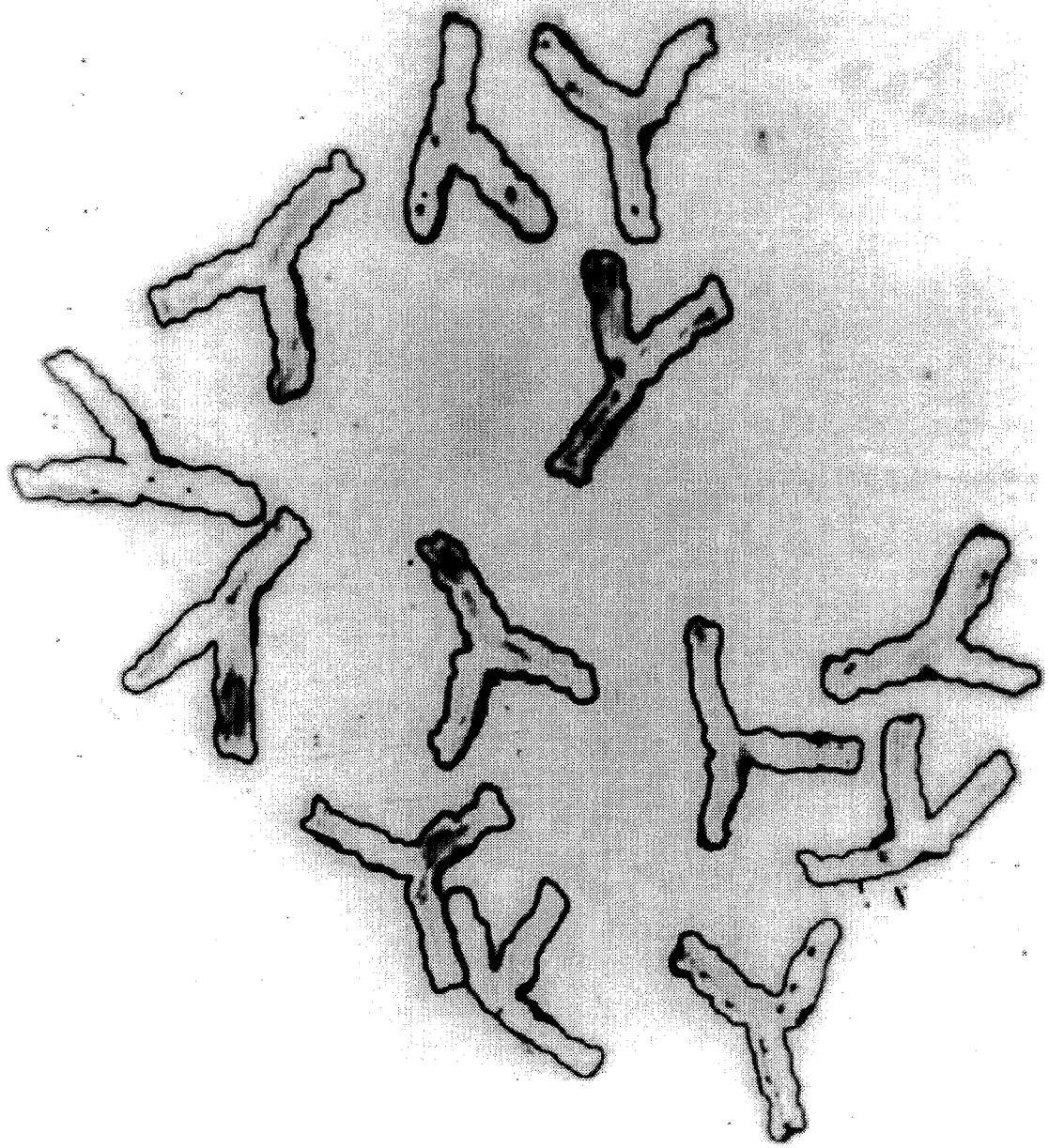

The cross-sectional shapes of the resulting filaments is shown magnified 500 times in FIG. 2 and magnified 1240 times in FIG. 3. The solid filaments have a well-defined Y-shape with a much higher degree of regularity than the filaments described in UK Patent 1 333 047 mentioned above. The length-to-width aspect ratio of the resulting filaments was between 3:1 and 4:1. This aspect ratio is determined by measuring the length l and width w of the limbs as exemplified in FIG. 4. For each limb measured, one length measurement and three width measurements are taken. The widths are measured at approximately the middle and at either end of the limb and then the average width of the limb is calculated from these three measurements. The aspect ratio is given as the ratio of the length l to average width w. Using the standard test defined in BP 1980, SDM.XI.A, p.128, the staple fibre was found to have a total free absorbency (TFA) of 25.6 gram of water per gram of fibre. The fibre also possessed an average water imbibition of 120%, a filament tenacity of 18 cN/tex and an extensibility of 23.5%.

To determine the water imbibition value of the filaments, a 1 g sample of dried filaments is soaked in water at a temperature of 20° C. for 15 minutes, centrifuges at a force of 10,000 Newton for 5 minutes, weighed, dried at a temperature of 110° C. for 2.5 hours and finally reweighed. Water imbibition is then defined as follows:

$$\frac{\text{weight of wet filaments} - \text{weight of dry filaments}}{\text{weight of dry filaments}} \times 100\%$$

Example 2

Figure 5:
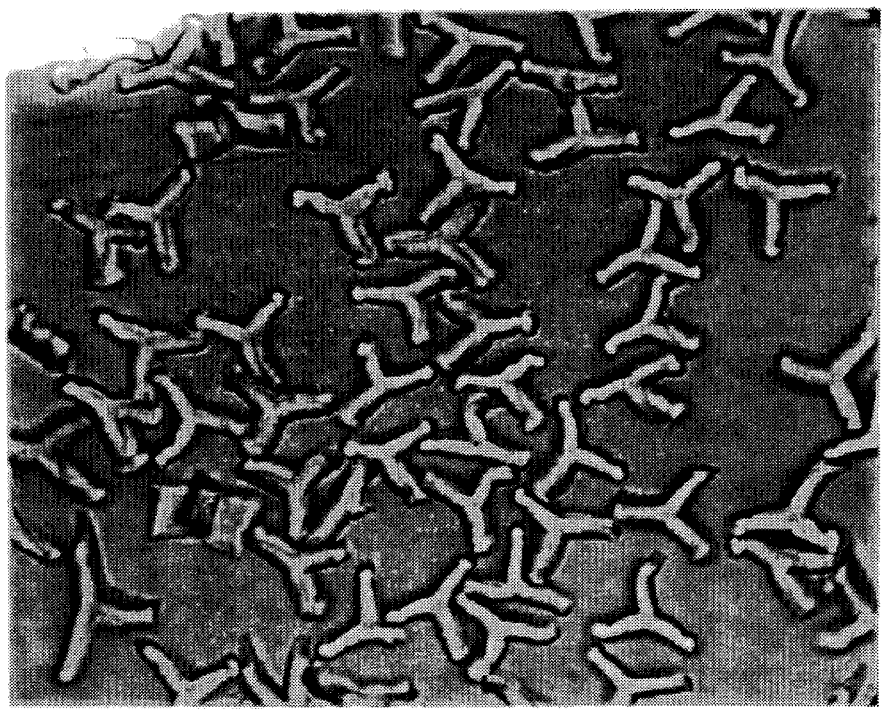

Y-shaped viscose fibre was produced as described in Example 1 with the following modifications:
Viscose salt figure: 6.0
Viscose modifier : 3% PEG-1500 added to viscose prior to spinning (no modifier added in Example 1)
Zinc sulphate in spin bath : 1.5%
Tow Stretch 50% in air
Viscose extrusion rate 1359 ml/min The resulting filaments were solid and had a well-defined, uniform Y-shaped cross-section as can be seen from the photograph of the filaments, magnified 500 times, in FIG. 5. The filaments had a decitex of 2.8 and a limb aspect ratio of 3:1 to 4:1. Using the same test as in Example 1, the staple fibre have a TFA of 25.4 g/g and a water imbibition of 113%. The filament tenacity was 16.7 cN/Tex and the extensibility 21.5%.

Example 3

A 16,568 filament viscose tow having the same composition as that described in Example 1 was spun through Y-shaped extrusion holes, the dimension of the limbs being 70 μm long and 25 μm wide with equivalent limb-to-limb angles of 120°. The filaments were spun into a bath comprising 9.0% sulphuric acid, 0.5% zinc sulphate, 24.0% sodium sulphate and 66.2% water at 50° C. to form a two of filaments having an average decitex of 1.3. The spinning speed was 50 m/min and the viscose extrusion rate was 726 ml/min. The tow was stretched by 50% in a 2% aqueous sulphuric acid solution at 95° C., cut to a staple length of 38 mm and washed.

The resulting filaments were solid and had a well defined Y cross-section with a limb aspect ratio between 3:1 and 4:1. The staple fibre had a TFA of 25.8 g/g, a water imbibition of 125%, a filament tenacity of 18.3 cN/tex and an extensibility of 25.2%.

Example 4

A 14,364 filament viscose tow was produced as described in Example 3 except that the viscose was spun from Y-shaped extrusion holes with limbs 89 μm long and 25 μm wide and the viscose extrusion rate was 2184 ml/min to form a tow of filaments having an average decitex of 4.5.

The resulting solid filaments had a well defined Y cross-section with a limb aspect ratio above 2:1, a TFA of 26.0 g/g, a water imbibition of 104%, a filament tenacity of 19.0 cN/tex and an extensibility of 22.8%.

Example 5

Staple fibres produced as described in Examples 1 and 2 were each formed into two types of tampon: a longitudinally expanding tampon having an average weight of about 2.72 g and an average density of about 0.35 g/cm³ and a radially expanding tampon having an average weight of about 2.8 g and an average density of 0.45 g/cm³.

The surface properties of the fibre were modified by the addition of a glycerol finish in order to obtain a tampon having a stability of approximately 15 mm for the longitudinally expanding tampons, and approximately 3.5 to 7.0 decaNewtons (daN) for the radially expanding tampons.

The stability of a longitudinally expanding tampon is measured by the 'expansion test' whereby the tampon is measured by the 'expansion test' whereby the tampon is maintained in a controlled environment after manufacture and the increase in the length of the tampon in millimeters is measured.

The stability of a radially expanding tampon is measured using the 'crush test' which measures, in decaNewtons (daN), the longitudinal force required to buckle the tampon. The cylindrical tampon is placed with one end on fixed lower jaw of a test machine, the upper moveable jaw is brought down to contact the other end of the tampon and is then set to move down at a speed of 5 cm/min. The force exerted by the tampon on the jaws of the test machine is measured continuously and the point at which this force begins to fall instead of rise is the point at which the tampon buckles. The maximum force achieved is the stability of the tampon. During the test the tampon is maintained in a controlled environment of 65% RH and 20° C.

The absorbency of each tampon was then tested using a 'modified Syngina' test. For the radially expanding tampons the test used was as defined in UK Patent 2 094 637B, pp. 4–6 except that a 200 mm hydrostatic head air pressure was employed. For the longitudinally expanding tampons the test was used as defined in the said patent with the further modification that 1 180 mm hydrostatic head water pressure was employed, the Syngina chamber was tilted at 30° to the vertical and the saline solution was injected into the top of the tampon, using a hypodermic needle, at a rate of 50 mm/hour. For both tampon types the absorbency was tested with a 1% saline solution.

The absorbencies were compared with those of tampons formed from standard, circular cross-section viscose fibre spun from equivalent viscose compositions and spinning conditions and finished in order to obtain stability approximately 15 mm and 3.5 to 7.0 daN for longitudinally and radially expanding tampons respectively. The absorbencies were also compared with those of tampons formed from collapsed hollow viscose fibre produced according to UK Patent 1 333 047. The water imbibition of each fibre type was also measured.

The results are given in Tables A and B, where 'Y-shaped (1)' and 'Y-shaped (2)' denote tampons formed from the staple fibre of Examples 1 and 2 respectively, 'Standard (1)' and 'Standard (2)' denote tampons spun from standard staple viscose fibre produced from viscose compositions and using spinning conditions equivalent to those of Examples 1 and 2 respectively, and 'Collapsed Hollow' denotes a tampon produced from staple fibre according to UK Patent 1 333 047.

TABLE A

| | Longitudinally Expanding Tampon | | |
|---|---|---|---|
| Fibre Type | Absorbency (g/g) | Stability (mm) | Water Imbibition (%) |
| Y-shaped (1) | 4.35 | 15 | 120 |
| Standard (1) | 3.82 | 14 | 103 |
| Y-shaped (2) | 4.76 | 15 | 113 |
| Standard (2) | 3.96 | 15 | 88 |
| Collapsed Hollow | 4.47 | 12 | 270 |

The results in Table A show that longitudinally expanding tampons formed from the fibre according to the invention have, for a given stability, a much higher absorbency than tampons formed from equivalent standard viscose fibre. Furthermore, when the fibre of the invention is spun using a modified viscose composition as in Example 2, then the resulting tampon also has an absorbency higher than that achieved using collapsed hollow viscose fibre, even though the water imbibition of the collapsed hollow fibre is more than double that of the fibre of the invention.

TABLE B

Radially Expanding Tampon

| Fibre Type | Absorbency (g/g) | Stability (daN) | Water Imbibition (%) |
|---|---|---|---|
| Y-shaped (1) | 4.76 | 3.8 | 120 |
| Standard (1) | 3.98 | 3.5 | 103 |
| Y-shaped (2) | 5.53 | 7.0 | 113 |
| Standard (2) | 3.82 | 4.0 | 88 |
| Collapsed Hollow | 5.30 | 3.2 | 270 |

The results in Table B show that radially expanding tampons formed from fibre according to the invention have a markedly greater absorbency than tampons formed from standard fibre. This is particularly noticeable when 'Y-shaped (2)' fibre is used as this tampon has superior absorbency as well as superior stability over tampons formed from both standard and collapsed hollow viscose fibre.

Example 6

The staple fibres of Examples 1 and 2 were each formed into tampons as described in Example 5 except that no finish was added to the fibre to modify its surface properties, and hence no alteration was made to the 'natural' stability of the tampons.

These stabilities were compared with those of tampons from unfinished equivalent standard viscose fibres. The results are given in Table C.

TABLE C

| Fibre Type | Tampon Type | Stability |
|---|---|---|
| Y-shaped (1) | Radially Expanding | 5.4 daN |
| Standard (1) | Radially Expanding | 3.6 daN |
| Y-shaped (1) | Longitudinally Expanding | 9 mm |
| Standard (1) | Longitudinally Expanding | 16 mm |
| Y-shaped (2) | Radially Expanding | 7.0 daN |
| Standard (2) | Radially E:Kpanding | 4.0 daN |
| Y-shaped (2) | Longitudinally Expanding | 7 mm |
| Standard (2) | Longitudinally Expanding | 15 mm |

These results show that for both tampon types, the fibre according to the invention has considerably greater stability than standard fibre., This is especially evident in tampons formed from fibre type 'Y-shaped (2)'.

Example 7

A viscose having the same composition as that described in Example 1 was spun through Y-shaped extrusion holes as specified in Example 1, into a spin bath comprising 10.,5% sulphuric acid, 0.7% zinc sulphate, 24.0% sodium sulphate and 64.8% water to form a two of Y-shaped filaments having an average filament decitex of 2.4 and a limb aspect ratio between 3:1 and 4:1. The tow was stretched by 50% in a 2% aqueous sulphuric acid solution at 95° C., cut to staple lengths of 38 mm, washed and dried.

The resulting fibre was blended with a 1.7 decitex polyester, 'SD Grilene B', to form a 50% viscose, 50% polyester by weight yarn having a 1/30 s cotton count. The fibre was made up into a knitted fabric with a dropped needle interlock construction. The fabric weighed 340 g/m and had a thickness of 2.0 mm.

The rate of absorbency, bulk, drapability, and flexural rigidity of the fabric were measured using the following tests:

Rate of absorbency: This was measured using the 'Plate Test' as defined in a paper entitled 'A Survey and Comparison of Laboratory Test Methods for Measuring Wicking' by P. R. Harnett and P. N. Mehta, Textile Research Journal, July 1984, pp 471–4713. The fabric was washed and immersed in water and the amount of water absorbed was measured at intervals over 2 minutes.

Bulk: The rate of air flow through a 5 g compressed sample of the fabric was measured on a manometer using the Shirley Micronaire test method, the lower the rate the greater the fabric bulk.

Drapability: The drapability of a fabric is the extent to which it will deform when it is allowed to hand under its own weight. Drapability was measured by determining the drape coefficient of the face and back of the fabric, drape coefficient being the ratio of the projected area of the draped specimen to its undraped area, according to BSI test BS 5058 1973.

Flexural Rigidity: The degree to which the fabric bends under its own weight was measured according to BSI test BS 3356 1961. The flexural rigidity along the length and across the width of the fabric was determined.

The fabric properties were compared with an equivalent standard viscose/polyester knitted fabric wherein the viscose fibre was spun from an equivalent composition and using the equivalent spinning conditions as above except that the filaments were spun through standard, circular cross-section holes.

The results are given in Tables D, E. and F, where 'Y-shaped' denotes the fabric containing Y-shaped viscose fibre and 'Standard' denotes the fabric containing the standard, circular cross-section viscose fibre.

TABLE D

Fabric Absorbency

| | Absorbency (cm³/g) | |
|---|---|---|
| Time (secs) | Y-shaped | Standard |
| 15 | 1.53 | 0.22 |
| 30 | 1.88 | 0.62 |
| 60 | 2.10 | 1.35 |
| 90 | 2.17 | 1.63 |
| 120 | 2.19 | 1.77 |

These results show that fabric containing fibre according to the invention has a substantially improved rate of absorbency over equivalent fabric containing standard viscose fibre.

TABLE E

Fabric Bulk

| Fabric Type | Air Flow (cm³/sec) |
|---|---|
| Y-shaped | 16.6 |
| Standard | 24.4 |

The air flow through the fabric containing the Y-shaped fibre is considerably lower than the air flow through the standard fabric which shows the higher bulk of the fabric containing fibre according to the invention.

TABLE F

Drapability and Flexural Rigidity

|  |  | Y-Shaped | Standard |
|---|---|---|---|
| Drape coefficient: | face | 0.118 | 0.087 |
|  | back | 0.126 | 0.106 |
| Flexural rigidity: | length | 40.0 | 27.3 |
|  | width | 17.2 | 9.3 |

The higher drape coefficient and higher flexural rigidity of the fabric containing the Y-shaped fibre indicates that this fabric has a stiffer, more cotton-like handle than standard viscose fabrics.

Example 8

From fibre produced under the conditions specified in Example 1, latex bonded nonwovens were prepared using a Kidd & Zigrino saturation bonder. A VA/E vinyl acetate-ethylene copolymer (type R32440) (available from Vinamul Limited) was used as the binder at 20% add-on to 100% viscose webs. The bonded fabrics were produced at 40 gsm and evaluated using the following tests:

Bulk: the average thickness of the 40 gsm fabric in mm using the EDANA recommended test for nonwoven thickness 30.2–78.

Overall Dry Strength: the maximum load sustainable by the fabric using the EDANA recommended test for nonwoven tensile strength 20.0–73, where the overall dry strength is taken to be the square root of the product of the individual machine and cross-directional strengths.

Absorbent Capacity: the quantity of water retained by a 4 cm diameter circle of the fabric after total immersion for one minute and draining for 30 secs, in g/g.

Wicking Distance: the capillary water rise (speed of liquid transport) in mm using the EDANA recommended test for nonwoven absorption 10.0–72.

The fabric properties were compared with an equivalent latex bonded fabric produced from standard circular cross-section viscose spun under identical conditions as given for the standard fibre in Example 7.

The results are given in Table G below, where 'Y-shaped' denotes the fabric containing Y-shaped fibre and 'Standard' denotes the fabric containing the standard, circular cross-section viscose.

TABLE G

| Property |  | Y-shaped | Standard |
|---|---|---|---|
| Bulk (mm) |  | 0.23 | 0.17 |
| Overall Dry Strength (daN) |  | 2.2 | 2.4 |
| Absorbent Capacity (g/g) |  | 10.6 | 7.3 |
| Wicking Distance (mm) at | 30 secs | 8 | 3 |
|  | 60 secs | 11 | 6 |
|  | 180 secs | 19 | 13 |

Example 9

From fibre produced under the conditions specified in Example 1, water jet entangled nonwovens were prepared using a Honeycomb hydroentanglement rig from 100% Viscose webs. The water pressure used to attain full entanglement was of the order of 1500 pse (10,000 kPa).

The bonded fabric was produced at 40 gsm and evaluated using the test methods described in Example 8.

The fabric properties were compared with an equivalent hydroentangled fabric produced from standard circular cross-section viscose spun under identical conditions as given for the standard fibre in Example 7.

The results are given in Table H below, where 'Y-shaped' denotes the fabric containing Y-shaped fibre and 'Standard' denotes the fabric containing the standard, circular cross-section viscose.

TABLE H

| Property |  | Y-shaped | Standard |
|---|---|---|---|
| Bulk (mm) |  | 0.22 | 0.18 |
| Overall Dry Strength (daN) |  | 1.3 | 1.3 |
| Absorbent Capacity (g/g) |  | 17.5 | 11.9 |
| Wicking Distance (mm) at | 30 secs | 5 | 3 |
|  | 60 secs | 7 | 5 |
|  | 180 secs | 12 | 8 |

The results given in Tables G and H indicate that for both latex and hydroentangled nonwovens the Y-shaped fibre produces bulkier, more absorbent products which are more able to transport fluid. In hydroentangled nonwovens Y cross-section fibre has the advantage of producing a fabric with stiffer, more cotton-like handle.

Example 10

From fibre produced under the conditions specified in Example 7, 100% viscose woven fabrics were prepared. The staple fibre was spun into a yarn having a 1/30's cotton count. The yarn was made up into a woven fabric with a 2×2 twill construction. The fabric weighed 320 gsm and had a thickness of 1.8 mm.

The fabric properties were compared with an equivalent standard viscose woven fabric wherein the viscose fibre was spun from an equivalent composition viscose as the Y-shaped fibre using identical spinning conditions. The results are quoted below for both fabrics following an evaluation using the test methods outlined previously in Example 7, where 'Y-shaped' again denotes the fabric containing the Y-shaped viscose fibre and 'Standard' denotes the fabric containing the standard, circular cross-section viscose fibre.

TABLE J

| Property |  | Y-shaped | Standard |
|---|---|---|---|
| Absorbency (cm³/g) at | 5 secs | 0.96 | 0.57 |
|  | 15 secs | 1.38 | 1.15 |
|  | 30 secs | 1.64 | 1.44 |
|  | 60 secs | 1.75 | 1.67 |
|  | 120 secs | 1.78 | 1.71 |
| Air Flow (cm²/sec) |  | 14.7 | 18.6 |
| Flexural Rigidity (mg · cm) | length | 53.0 | 45.4 |
|  | width | 27.1 | 23.7 |

The results show that fabric woven from the Y-shaped viscose fibre has improved properties over fabric woven from standard, circular cross-section viscose fibre.

Example 11

Figure 6:
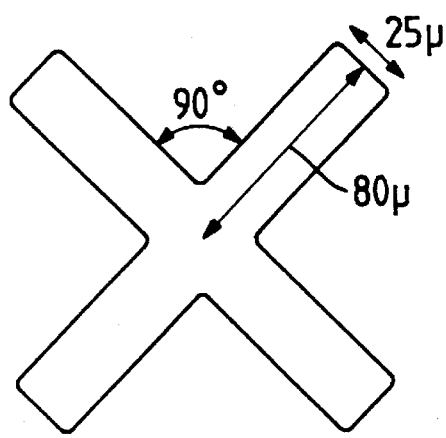

A 5000 filament viscose tow having the same composition as that described in Example 1 was spun through X-shaped extrusion holes, the dimensions of the limbs being 80 μm long and 25 μm wide, with equivalent limb to limb angles of 90° as shown in FIG. 6. The filaments were spun into a bath comprising 9.5% sulphuric acid, 1.0 zinc sulphate, 24.5% sodium sulphate and 65.0% water at 50° C. to form a tow of filaments having an average decitex of 3.5. The spinning speed was 50 m/min and the viscose extrusion rate was 590 ml/min. The tow was stretched by 50% in a 2% aqueous sulphuric acid solution at 95° C., cut to a staple length of 38 mm and washed.

The resulting solid filaments had a well defined X cross-section, with a limb aspect ratio of between 2:1 and 4:1. The staple fibre had a TFA of 25.0 g/g, a water imbibition of 114%, a filament tenacity of 19.0 cN/tex and an extensibility at break of 25.0%.

Example 12

X-shaped fibre was produced as described in Example 11 with the following modifications:
viscose salt figure: 6.0
viscose modifier: 3% PEG-1500 added to the viscose prior to spinning.
zinc sulphate in the spin bath: 1.5%.

Figure 7:
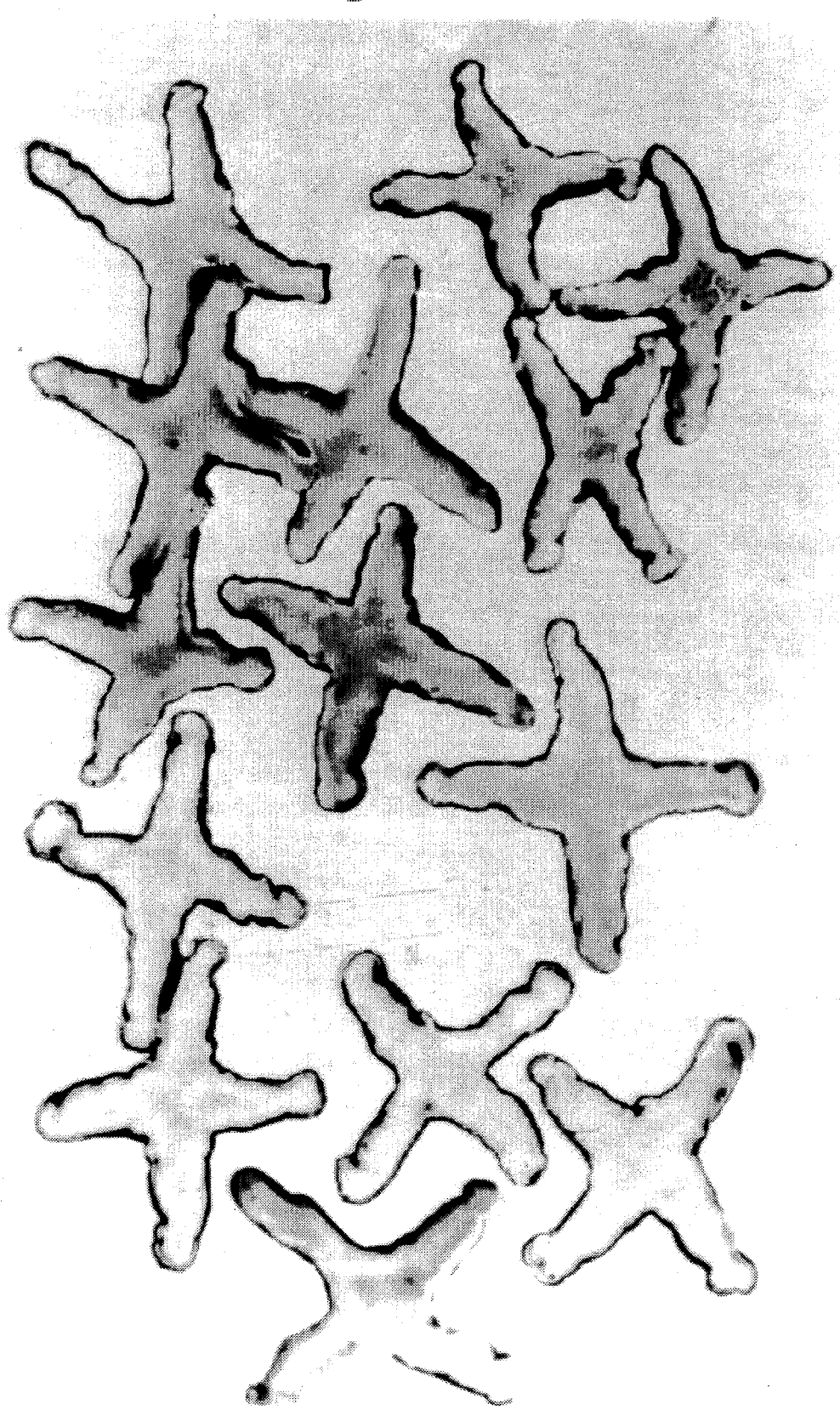

The resulting filaments were solid and had a well defined, uniform X-shaped cross-section as can be seen from the photograph of the filaments, magnified 1624 times, in FIG. 7. The filaments had a decitex of 3.5 and a limb aspect ratio of 3:1 to 4:1. The staple fibre had a TFA of 25.0 g/g and a water imbibition of 107%. The filament tenacity was 16.7 cN/tex and the extensibility was 25.0%.

Example 13

Staple X-shaped fibres prepared according to the conditions specified in Examples 11 and 12 were evaluated in longitudinally expanding tampons against standard circular cross-section viscose fibres produced under identical conditions, using the method outlined in Example 5. The surfaces of the fibres were modified by the addition of glycerol finish in order to obtain a tampon having a stability of approximately 15 mm.

The tampon absorbency values were also compared with those for tampons formed from collapsed hollow fibres produced according to UK Patent 1 333 047. The water imbibition of each fibre is specified.

The results are given in Table K below, where 'X-shaped' and 'X-shaped (M)' refer to tampons formed from the staple fibre of Examples 11 and 12 respectively. 'Standard' and 'Standard (M)' denote tampons produced from standard staple viscose fibre spun from viscose compositions and using spinning conditions equivalent to those of Examples 11 and 12 respectively. 'Collapsed Hollow' denotes a tampon produced from staple fibre according to the previously cited patent.

TABLE K

| Fibre Type | Absorbency (g/g) | Stability (mm) | Water Imbibition (%) |
|---|---|---|---|
| X-shaped | 4.26 | 14 | 114 |
| Standard | 3.80 | 15 | 100 |
| X-shaped (M) | 4.64 | 14 | 107 |
| Standard (M) | 3.85 | 15 | 94 |
| Collapsed Hollow | 4.47 | 12 | 270 |

Similar trends are observed to those described in Example 5.

Example 14

Figure 8:
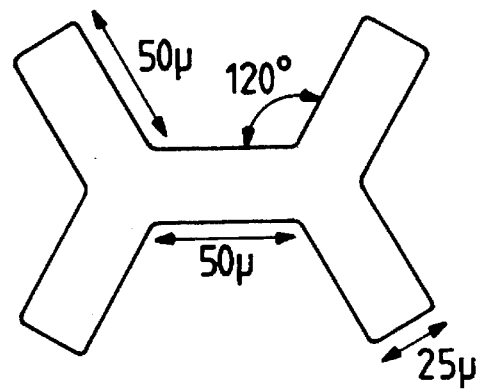

A 5000 filament viscose tow having the same composition as that described in Example 12 was spun through extrusion holes having a shape and dimensions as shown in FIG. 8.

The filaments were spun into a bath comprising 7.5% acid, 1.2% zinc and 23.5% sulphate at 50° C. to form a tow of filaments having an average decitex of 3.3. The spinning speed was 50 m/min and the viscose extrusion rate was 558 ml/min. The tow was stretched by 50% in air, cut to staple length of 38 mm and washed.

Figure 9:
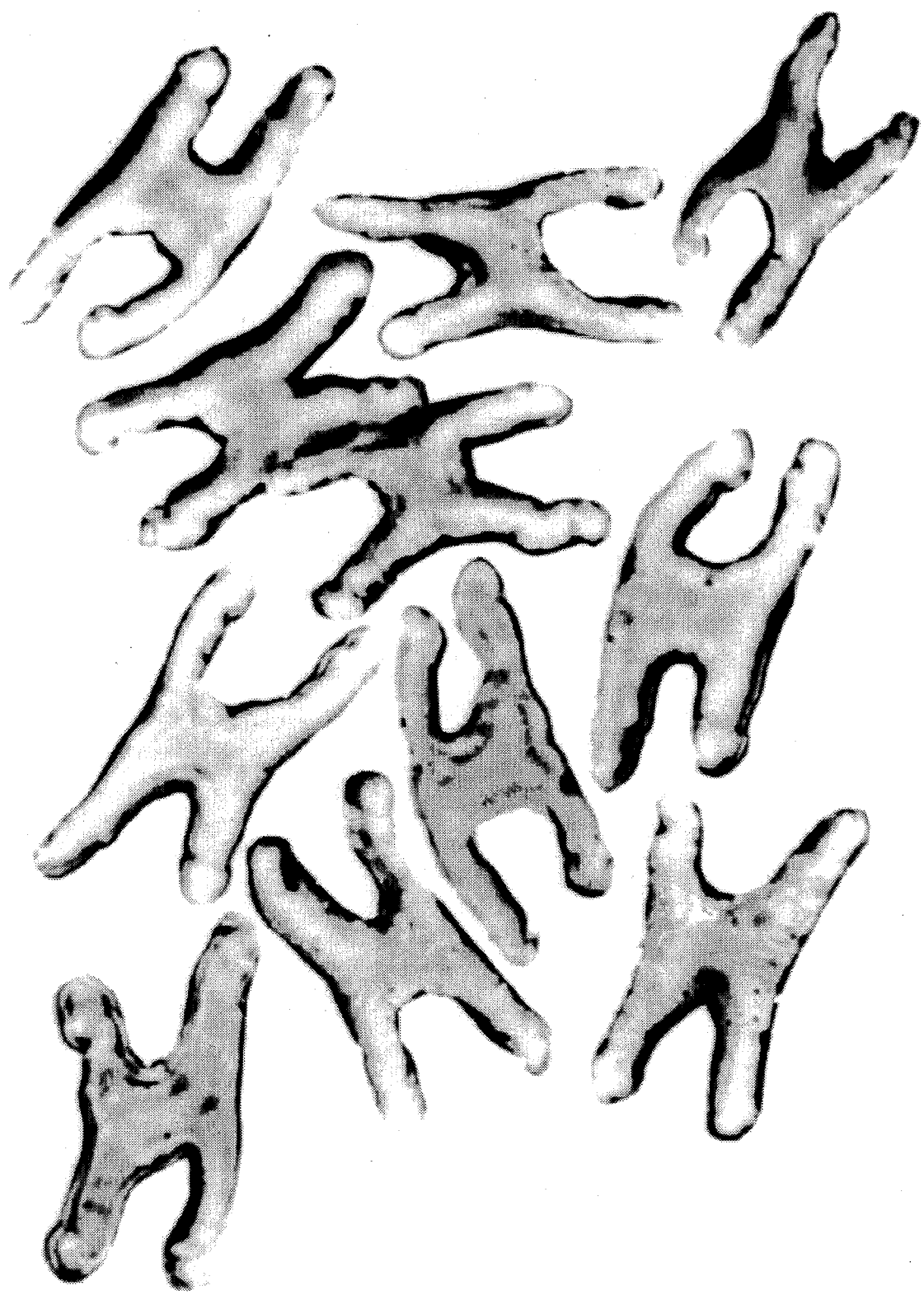

The resulting solid filaments had a well defined H-shaped cross-section as shown in FIG. 9, magnified 1624 times. The limb aspect ratio was between 2:1 and 4:1. The staple fibre had a TFA of 25.3 g/g, a water imbibition of 110%, a filament tenacity of 18.4 cN/tex and an extension of 23%.

What is claimed is:

1. A method of manufacturing solid cellulosic regenerated viscose staple fibre having a decitex in the range 0.5 to 5.0, said staple fibre having a multi-limbed cross-sectional shape comprising at least three limbs, each said limb having a length-to-width aspect ratio in the range 2:1 to 10:1, said method including the steps in sequential order of:

(a) extruding viscose through a spinnerette defining a plurality of multi-limbed extrusion holes into a spin bath comprising 6 to 20 percent by weight sulphuric acid, 0 to 3 percent by weight zinc sulphate and 10 to 28 percent by weight sodium sulphate thereby forming a tow of solid cellulosic regenerated viscose filaments, each said extrusion hole having a cross-sectional shape which is similar to said multi-limbed cross-sectional shape of said staple fibre;

(b) stretching said tow of filaments;

(c) cutting said tow of filaments to form staple fibre;

(d) washing said staple fibre; and (e) drying said staple fibre.

2. The method of claim 1 wherein said aspect ratio of each said limb is in the range 2:1 to 7:1.

3. The method of claim 2 wherein said aspect ratio of each said limb is in the range 3:1 to 5:1.

4. The method of claim 1 wherein said decitex of said staple fibre is in the range 1.5 to 4.0.

5. The method of claim 1 wherein the cross-sectional shape of said extrusion holes is selected from the group consisting of Y-, X-, H- and T-shapes.

6. The method of claim 1 wherein the cross-sectional shape of maid extrusion holes is Y-shaped.

7. The method of claim 1 wherein said viscose comprises a modifier.

8. The method of claim 7 wherein said modifier is polyethylene glycol.

9. The method of claim 8 wherein the average molecular weight of said polyethylene glycol is about 1500.

10. The method of claim 8 wherein said viscose comprises about 3 percent, by weight of said polyethylene glycol.

11. The method of claim 1 wherein said viscose comprises 5 to 12 percent by weight cellulose and 4 to 10 percent by weight caustic soda.

12. The method of claim 1 wherein said viscose has a salt figure in the range 4.0 to 12.0.

13. The method of claim 1 wherein said spin bath comprises 0.5 to 2.0 percent by weight of said zinc sulphate.

14. The method of claim 1 wherein the cross-section of each said multi-limbed extrusion hole defines a plurality of limbs, each said limb having a length in the range 50 to 250 micron and a width in the range 20 to 40 micron.

15. The method of claim 1 wherein the speed of said tow of filaments after said stretching step and prior to said cutting step is about 50 m/min.

16. The method of claim 1 wherein said tow of filaments is stretched in said stretching step by about 50 percent.

17. The method of claim 1 wherein said staple fibre has three or four limbs.

18. A method of manufacturing regenerated viscose staple fibre, said staple fibre consisting of a plurality of three-limbed individual fibres having a decitex in the range 0.5 to 5.0, including the steps in sequential order of:
(a) extruding a standard viscose composition through a spinnerette into a standard viscose spin bath composition under standard viscose spinning conditions to form a tow of regenerated viscose filaments, said spinnerette defining a plurality of extrusion holes, each said extrusion hole being of three-limbed cross-section;
(b) stretching said tow of filaments;
(c) cutting said tow of filaments to form staple fibre;
(d) washing said staple fibre; and
(e) drying said staple fibre,
whereby essentially all of said three-limbed individual fibres have essentially the same cross-sectional shape wherein the length-to-width aspect ratio of essentially all of said limbs of said three-limbed individual fibres is in the range 2:1 to 10:1.

19. The method of claim 18 wherein essentially all of said individual fibres exhibit a Y-shaped cross-section.

20. The method of claim 18 wherein essentially all of said individual fibres exhibit an essentially regular cross-section.

21. The method of claim 18 wherein said length-to-width aspect ratio is In the range 2:1 to 7:1.

22. The method of claim 21, wherein said length-to-width aspect ratio is in the range 3:1 to 5:1.

23. The method of claim 18 wherein said decitex is in the range 1.5 to 4.0.

24. The method of claim 18 wherein said standard viscose composition comprises a modifier.

25. The method of claim 24 wherein said modifier is polyethylene glycol.

26. The method of claim 25 wherein the average molecular weight of said/polyethylene glycol is about 1500.

27. The method of claim 24 wherein said standard viscose composition comprises about 3 percent by weight of said polyethylene glycol.

28. The method of claim 18 wherein each limb of each said three-limbed extrusion hole has a length in the range 50 to 250 micron and a width in the range 20 to 40 micron.

* * * * *

UNITED STATES PATENT AND TRADEMARK OFFICE
CERTIFICATE OF CORRECTION

PATENT NO. : 5,458,835

DATED : October 17, 1995

INVENTOR(S) : Andrew G. Wilkes and Alan J. Bartholomew

Page 1 of 2

It is certified that error appears in the above-indentified patent and that said Letters Patent is hereby corrected as shown below:

Col. 1, line 20, delete "&-shaped" and insert thereof -- Y-shaped --.

Col. 1, line 25, delete "from" and insert thereof -- form --.

Col. 1, line 31, after "filaments", insert -- , --.

Col. 4, line 12, delete "two" and insert thereof -- tow --.

Col. 4, line 49, delete "centrifuges" and insert thereof -- centrifuged --.

Col. 5, line 18, delete "two" and insert thereof -- tow --.

Col. 5, line 57, delete the second occurrence of the words "measured by the 'expansion test' whereby the tampon is".

Col. 7, line 55, delete "two" and insert thereof -- tow --.

Col. 8, line 6, delete "471-4713" and insert thereof -- 471-478 --.

UNITED STATES PATENT AND TRADEMARK OFFICE
CERTIFICATE OF CORRECTION

PATENT NO. : 5,458,835
DATED : October 17, 1995
INVENTOR(S) : Andrew G. Wilkes and Alan Bartholomew It is certified that error appears in the above-indentified patent and that said Letters Patent is hereby corrected as shown below:

Col. 9, line 65, delete "pse" and insert thereof -- psi --.

Col. 10, line 25, after the word "with", insert -- a --.

Col. 10, line 37, start a new paragraph with the word "The".

Col. 10, in Table J, line 53, move "14.7" under the appropriate column heading of "Y-shaped" and "18.6" under the appropriate column heading of "Standard".

Col. 14, line 14, claim 26, delete "/" after the word "said".

Signed and Sealed this

Eighteenth Day of June, 1996

*Attest:*

BRUCE LEHMAN

*Attesting Officer*     Commissioner of Patents and Trademarks